United States Patent [19]
Serfaty

[11] Patent Number: 5,636,987
[45] Date of Patent: Jun. 10, 1997

[54] APPARATUS AND INSTRUMENT FOR THE ELIMINATION OF SUBGINGIVAL BACTERIA

[76] Inventor: Raphaël Serfaty, 23, boulevard Saint-Martin, 75003 Paris, France

[21] Appl. No.: 370,328

[22] Filed: Jan. 10, 1995

[30] Foreign Application Priority Data

Jul. 20, 1993 [FR] France .................. 93 08899

[51] Int. Cl.$^6$ ........................... A61G 17/02
[52] U.S. Cl. .............. 433/80; 601/162; 601/165
[58] Field of Search .............. 433/80, 88, 216; 601/162, 165; 251/6

[56] References Cited

U.S. PATENT DOCUMENTS

| | | | |
|---|---|---|---|
| 3,496,933 | 2/1970 | Lloyd | 601/162 |
| 4,458,877 | 7/1984 | Holmes | 251/6 X |
| 4,911,399 | 3/1990 | Green | 251/6 |
| 4,919,389 | 4/1990 | Hoekwater et al. | 251/6 |
| 4,941,459 | 7/1990 | Mathur | 601/165 |
| 4,974,811 | 12/1990 | Ishida | 251/6 |
| 5,218,956 | 6/1993 | Handler et al. | 601/162 X |

FOREIGN PATENT DOCUMENTS

| | | |
|---|---|---|
| 0163156 | 12/1985 | European Pat. Off. . |
| 2565816 | 12/1985 | France . |
| 3708736 | 10/1988 | Germany . |
| 3801097 | 7/1989 | Germany . |
| 8502240 | 5/1985 | WIPO . |

*Primary Examiner*—Nicholas D. Lucchesi
*Attorney, Agent, or Firm*—Browdy and Neimark

[57] ABSTRACT

Dental treatment instrument adaptable to a pulsed liquid generator constituted by a handpiece comprising a compressible tube (13) at least one section of which is accessible to a compression element (20), said compressible tube establishing fluid communication between an irrigation liquid feed and an irrigation liquid outlet (3) which is either an irrigation catheter (10), or an attachment system (15, 17), of such a catheter and dental treatment apparatus provided with such an instrument.

17 Claims, 2 Drawing Sheets

APPARATUS AND INSTRUMENT FOR THE ELIMINATION OF SUBGINGIVAL BACTERIA

FIELD OF THE INVENTION

The present Application relates to a new professional apparatus and instrument for the elimination of subgingival bacteria with the aim of treating inflammation associated with parodontal, endodontic, traumatic or infectious lesions.

REVIEW OF THE RELATED ART

Parodontal disease is characterized by the formation, along the tooth, of a more or less deep cavity, which puts the root in direct contact with an accumulation of pathogenic bacteria.

At present no apparatus and instrument exists which allows the irrigation of this cavity of less than 3 mm wide using an irrigation liquid under favourable conditions, in particular with precision, and at a reasonable price.

The ideal instrument should be easy to handle, free from vibrations and sterilizable; it should allow the operator, i.e. the dentist or stomatologist, to concentrate solely on his work without having having to look anywhere else other than at the tooth to be treated, and to run no risk of causing an additional traumatism by excess pressure of the irrigation liquid or using the needle at an incorrect angle. In fact, the use of such a needle in a cavity characteristic of parodontal disease is delicate, even for a well-trained professional, considering the apparatuses currently on the market.

FR-A-2,565,816 describes a special socket adaptable to any of the existing hydro-pulse machines, to any drive connection, any roller pump, or any apparatus containing a supply of air and water with an intermediate connecting element, said socket containing a hollow catheter having a rounded end allowing insertion and irrigation under the gum.

However, such a socket in particular transmits the vibrations of the hydro-pulse machine and an action on the controls situated on this machine is required when one wishes to modify or stop the irrigation jet; this runs the risk of cross contamination.

Also "general public" apparatuses are known DE-A-3, 708,736 and 3,801,097 as well as from EP-A-0,163,156 which are used for cleaning teeth and the gaps between teeth fitted with a very rigid tube, which allows a violent and spasmodic jet to be propelled at a pressure of the order of 400 to 450 mm of mercury. The pulsed liquid generator is preferably the apparatus commonly called a "hydro-pulse machine". A standard hydro-pulse machine includes a reservoir and a pump which takes the liquid from the reservoir, in order to propel it in pulses, under pressure, towards the sockets, via a tube with rigid and usually spirally wound walls. The attachment of a simple catheter to the end of such a tube does not allow professional use under acceptable conditions of comfort and safety.

SUMMARY OF THE INVENTION

This is why a subject of the present Application is a dental treatment apparatus characterized in that it is constituted by a generator producing a pulsed liquid connected using a tube made of thin elastic material, having a length greater than 50 cm, to an elongated instrument, establishing fluid communication between the liquid originating from the pulsed liquid generator and one end of the instrument, said end of the instrument containing a hollow catheter or an adaptation system for a hollow catheter for irrigating the subgingival cavity.

The tube made of elastic material used in the present invention, taking into account the length and flexibility of its material, transmits practically no vibration to the elongated instrument, i.e., it has a high damping coefficient, which is a means for damping pulsations inside the tube.

By "elastic material" is meant a material which is extensible and compressible using moderate force.

For example, a tube made of silicone plastic material can be used such as that marketed by the company AIREL under the reference "Silicone origine Rhôe Poulenc".

The external diameter of the tube can range for example from 3 to 7 mm, and is preferably about 4 to 5 mm for a thin-walled thickness of, for example, 0.3 to 0.9 mm, in particular 0.4 to 0.8 mm, preferably about 0.5 to 0.8 mm.

Its length can range, for example, from 0.5 to 2 m and preferably from about 1.5 to 2 m.

By "elongated instrument" is meant an instrument, for example, with a length of 10 cm or more, for a section of 1 cm; the instrument advantageously has the shape and dimensions of a pen, optionally curved.

In order to allow the flow of irrigation liquid to be stopped without the attention of the operator having to leave the gum, the elongated instrument advantageously includes an adjustment means for the flow rate of the liquid circulating towards the catheter, which is preferably a compressible tube of which at least one section is accessible to a compression element, said compressible tube establishing fluid communication between an irrigation liquid feed and an irrigation liquid outlet which is either an irrigation catheter, namely a hollow needle with a blunt end, or an attachment system, for example by screw or bayonet fitting or by simple clamping of such a catheter.

The compression element can be one of the operator's fingers, flattening the compressible tube. It can be any appropriate mechanical device, and advantageously a roller wheel which is displaceable preferably along the longitudinal axis of the elongated instrument using a guiding structure constituted by at least one guide allowing the compression of said compressible tube.

In order to limit the pressure of the liquid at the irrigation socket, the new apparatus according to the invention contains advantageously a pressure limiting system which is constituted by a branch connection in the tube connecting the hydro-pulse machine to the instrument, for example a so-called "T-piece". The pressure obtained is of the order of 40 to 80 mm of mercury, and in particular about 60 mm of mercury.

This branch connection is itself advantageously provided with a return pipe bringing a portion of the liquid originating from the pulsed liquid generator into a reservoir from which this pumps the liquid.

Such a device allows, in addition to limiting the pressure below a traumatizing value, permanent agitation and mixing of the liquid in the reservoir of the hydro-pulse machine, in this way introducing oxygen molecules from the air to which the anaerobic bacteria are sensitive.

The end of the return pipe advantageously includes a ballast the essential function of which is to maintain the end of the return pipe on or near the bottom of the reservoir.

Advantageously the end of the return pipe includes a system for the adjustment of the return flow, preferably situated on the ballast which also allows the maximum pressure of liquid in the catheter to be adjusted.

The two functions mentioned above are advantageously fulfilled by a single ballast element which is a weighty hollow element and therefore lies on the bottom of the reservoir, one end of the element being connected to the return pipe, the said element containing an adjustment screw allowing the closing of all or part, as desired, of the opening of said element.

Said element can also include perforations, indentations or similar on its periphery to ensure the return of liquid whatever the position. It can for example have the shape of a cylinder or a parallelepiped such as a cube.

In order to allow the best handiness of the instrument, the return branch connection is installed close to the hydro-pulse machine, for example, within 20 or 30 cm of the latter, while generally the length of the tube connecting the hydro-pulse machine to the instrument will be 50 cm to 2 metres and more, and advantageously from 1.5 to 2 metres.

In order to control the flow rate of the irrigation liquid in a satisfactory and straightforward manner, the elongated instrument advantageously includes a roller wheel allowing the tube to be flattened preferably inside the previously mentioned instrument connecting the tube, made of elastic material originating from the hydro-pulse machine, to the attachment system for a hollow irrigation catheter.

The embodiments of the adjustment or stopping of the flow are for example the following:

—the roller wheel is guided by one or more guides following a movement which either brings the roller wheel progressively closer to the internal tube until it is totally flattened and the circulation of the liquid is blocked, the internal tube being set in this case against an abutment for example parallel to said tube, or when the displacement of the roller wheel takes place parallel to the axis of the elongated instrument at this level while the tube co-operates with an abutment so as to progressively approach said axis. The same effect of pinching the tube is obtained in both cases.

The roller wheel for adjusting and stopping the flow is situated on the instrument, advantageously close to, for example 2 to 5 cm from the irrigation catheter, in order to allow easy manipulation for example with the thumb, index finger or middle finger.

Also a subject of the present invention is a dental treatment instrument specially designed for the dental treatment apparatus described above, characterized in that it is constituted by a handpiece comprising a compressible tube at least one section of which is accessible to a compression element, said compressible tube establishing fluid communication between an irrigation liquid feed and an irrigation liquid outlet which is either an irrigation catheter, namely a hollow needle with a blunt end, or an attachment system, for example by screw or bayonet fitting or by simple clamping of such a catheter.

The end of the instrument intended to carry the irrigation catheter advantageously includes an attachment system for said catheter allowing this to be fitted in a firm and watertight fashion to the end of the instrument.

This is why the end of the instrument advantageously includes either a thread, or a so-called "bayonet" system allowing the attachment and locking of a catheter.

Centered in the fixing and locking system one preferably finds an element in fluid contact with the compressible tube and the hydro-pulse machine, supplying the liquid to the catheter. This element is advantageously provided with a watertight system such as an O-ring seal. The compressible tube is advantageously inside the handpiece which preferably has the general shape of a tube or a pen, and can be optionally curved.

Other characteristics of the elongated instrument are set out above within the scope of the description of the treatment apparatus which is a subject of the invention, as well as hereafter in the examples.

The apparatus and the instrument according to the present invention have remarkable qualities.

Thanks to the attachment system with which the instrument according to the invention is provided, one can install in a removable manner all types of catheters or hollow needles, with various shapes, advantageously with a curved shape (for pre-surgical irrigation in buccal surgery and in bone implant surgery etc. . . ).

All the elements, including piping, catheter, instrument and its various parts are produced in sterilizable materials.

The combination of material, the dimensions of the latter and the length of piping connecting the hydro-pulse machine to the instrument according to the present invention avoids the transmission of vibrations to the instrument, leaving the practitioner a high degree of precision in medical actions, especially when access to the parodontal disease cavities and the bottom of the mouth is difficult.

BRIEF DESCRIPTION OF THE DRAWING

The invention will be better understood if reference is made to the attached drawings in which.

DETAILED DESCRIPTION OF THE PREFERRED EMBODIMENTS

Figure 1:
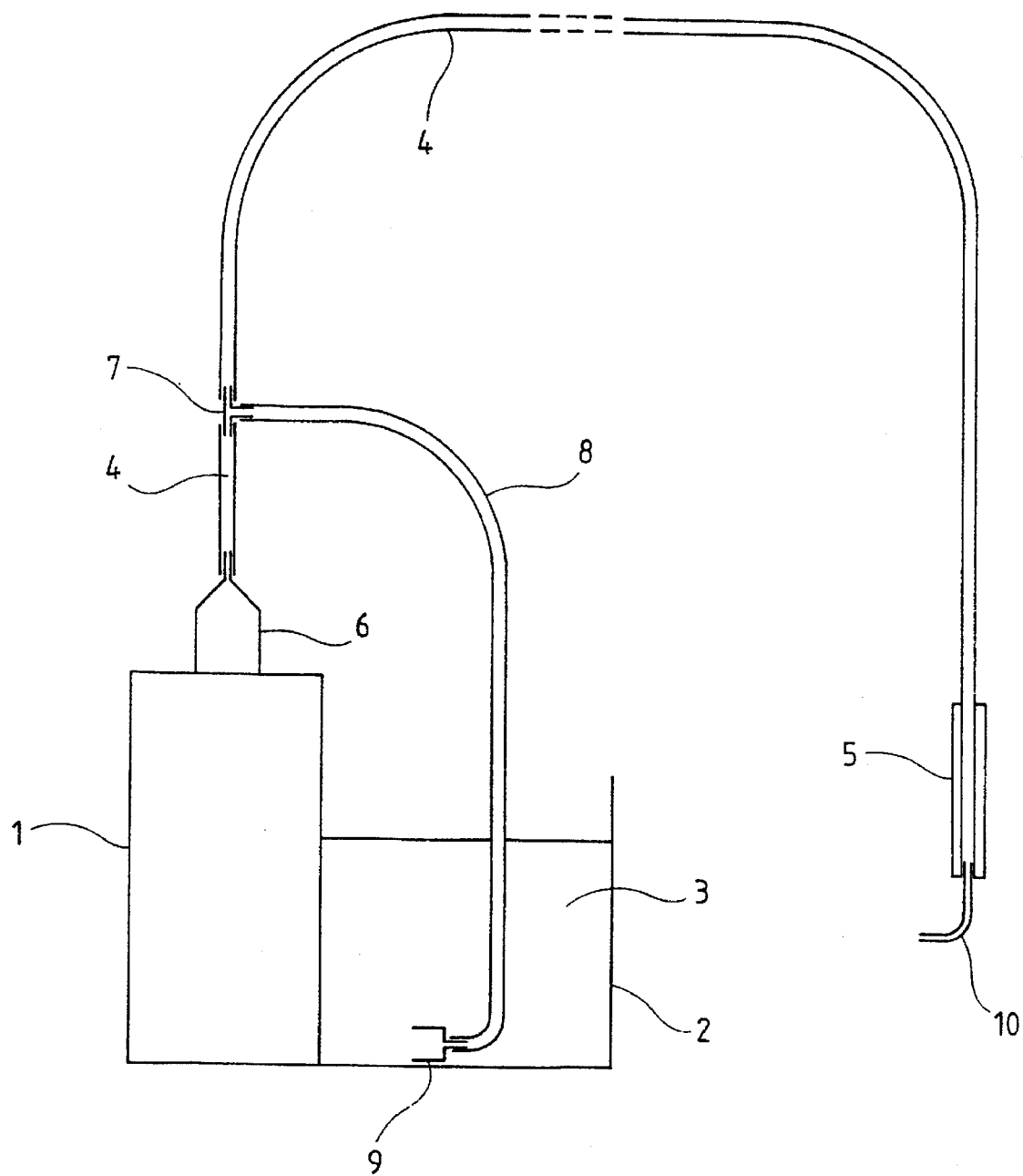
FIG. 1 is a schematic of the assembly apparatus according to the present invention and FIG. 2 represents an instrument according to the invention in longitudinal section.

In FIG. 1, one part of the hydro-pulse machine unit 1 can be seen, comprising a reservoir 2. The liquid 3 propelled by the unit is transported, via a flexible tube 4 made of silicone plastic material (internal diameter 1.5 mm, external diameter 3 mm, length 1.80 m) to the dental instrument 5.

One part of this tube 4 is connected to the liquid outlet of the hydro-pulse machine by an adapter 6 and includes, near to the hydro-pulse machine, a T-shaped branch connection 7 taking part of the flow into the reservoir 2 from which the liquid to be propelled is pumped via a return pipe 8 the end of which is provided with a ballast 9 resting on the bottom of the reservoir 2. The end of the instrument 5 is provided with an irrigation catheter 10.

Figure 2:
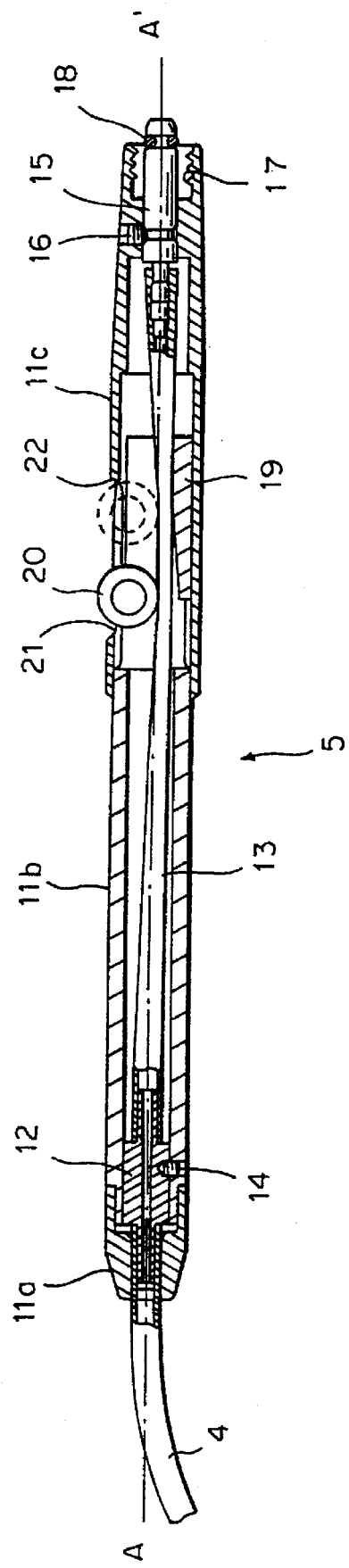

In the section of FIG. 2 which represents the instrument according to the invention, the handle of the instrument is seen which is composed of three pieces 11a, 11b, 11c. The tube 4 fixes onto the end of one of the two sockets of a joining piece 12 allowing the circulation of the liquid 3 in the tube 4 towards the internal tube 13 of the instrument, this piece 12 is firmly attached to part 11b of the handle using a small screw 14, the other end of the internal tube 13 is fixed to a socket of a second joining piece 15 firmly attached to one of the parts 11c of the handle using another small screw 16. The other socket, external to the instrument, of the second piece 15 also serves for the attachment of an irrigation catheter which is not shown here. This fixes to the end of piece 15 by insertion then screwing on the thread 17 provided on part 11b of the handle, watertightness is ensured by an O-ring seal 18 situated in a throat provided on the external socket of this piece 15. The internal tube 13 partially rests on an abutment 19 the thickness of which increases in the direction of the part of the instrument on which the catheter is fixed. A roller wheel 20 guided laterally parallel to axis AA' of the instrument and whose extreme displacements in the direction AA' are limited by stops 21 and 22, allows the adjustment of the flow rate of the liquid; represented here in solid lines, it allows the entire flow to pass. Displaced to the position represented by the dotted lines, it flattens the tube 13 against the abutment 19 so as to stop the flow.

What is claimed is:

1. A dental treatment instrument of the type including a hydro-pulse type pump, means for delivering supply water to the pump, a hollow irrigation catheter (10), a tube connecting the pump to the catheter to eject pumped water from a distal end of the catheter, and handpiece means for manipulating the catheter to irrigate the mouth; the improvement wherein the tube includes means for damping pulsations of the pump, whereby a non-pulsating stream of ejected water is discharged from the distal end of the catheter.

2. The improvement according to claim 1, wherein the means for damping pulsations comprises a tube length of at least approximately 1.5 meters.

3. The improvement according to claim 2, wherein the tube length is up to approximately 2.0 meters.

4. The improvement according to claim 1, wherein the means for damping pulsations comprises a tube wall thickness of less than approximately 0.8 millimeters.

5. The improvement according to claim 4, wherein the tube wall thickness is more than approximately 0.4 millimeters.

6. The improvement according to claim 2, wherein the means for damping pulsations comprises elastic tubing material.

7. The improvement according to claim 6, wherein the means for damping pulsations comprises tubing material having a large damping coefficient.

8. The improvement according to claim 7, wherein the tubing material comprises silicone.

9. The improvement according to claim 1, wherein the means for damping pulsations comprises means for reducing water pressure adjacent the distal end of the catheter to approximately of the order of 40 to 80 millimeters of mercury.

10. The improvement according to claim 1, wherein the handpiece means includes a handpiece comprising a compressible tube (13), at least one section of which is accessible to a compression element (20), said compressible tube establishing fluid communication between an irrigation water feed and an irrigation water outlet (3), the irrigation water outlet comprising the catheter (10).

11. The improvement according to claim 10, wherein the irrigation water outlet comprises an attachment system (15, 17) of the catheter.

12. The improvement according to claim 10, wherein the compression element is a mechanical compression device (20) for the compressible tube (13).

13. The improvement according to claim 12, wherein the mechanical compression device is a roller wheel (20).

14. The improvement according to claim 13, wherein the roller wheel co-operates with an abutment (19) situated opposite it in order to compress the compressible tube (13).

15. The improvement according to claim 10, wherein the compressible tube (13) is contained in an elongated instrument.

16. The improvement according to claim 1, comprising a branch connection to the tube, the branch connection including a return pipe bringing a portion of the water originating from the pulsed water generator into a reservoir from which water is pumped.

17. A dental treatment instrument of the type including a hydro-pulse type pump, means for delivering supply water to the pump, an elongated instrument, and a tube connecting the pump to the elongated instrument to eject pumped water from a distal end of the elongated instrument; the improvement wherein the tube includes means for transmitting minimal vibration to the elongated instrument, whereby a non-pulsating stream of ejected water is discharged from the distal end of the elongated instrument.

* * * * *